United States Patent [19]

Herrmann et al.

[11] 4,255,433

[45] Mar. 10, 1981

[54] (+)-(3-METHYL-4-OXO-5N-PIPERIDINO-THIAZOLIDIN-2-YLIDENE)ACETIC ACID ESTERS, METHOD OF PREPARATION AND USE

[75] Inventors: Wolfgang Herrmann, Merzhausen; Gerhard Satzinger, Denzlingen; Manfred Herrmann, St. Peter; Wolfgang Steinbrecher, Gundelfingen; Heinrich Bahrmann, Kirchzarten, all of Fed. Rep. of Germany

[73] Assignee: Godecke Aktiengesellschaft, Freiburg, Fed. Rep. of Germany

[21] Appl. No.: 132,577

[22] Filed: Mar. 21, 1980

[30] Foreign Application Priority Data

Mar. 22, 1979 [DE] Fed. Rep. of Germany ....... 2911296
Dec. 29, 1979 [DE] Fed. Rep. of Germany ....... 2952704

[51] Int. Cl.³ .................. A61K 31/445; C07D 417/04
[52] U.S. Cl. .................................... 424/267; 546/209
[58] Field of Search ........................ 546/209; 424/267

[56] References Cited

U.S. PATENT DOCUMENTS 3,072,653   1/1963   Satzinger et al. .................... 546/209
4,012,395   3/1977   Satzinger et al. .................... 546/209

Primary Examiner—John D. Randolph
Assistant Examiner—Robert T. Bond
Attorney, Agent, or Firm—Stephen I. Miller

[57] ABSTRACT

The invention discloses (+)-(3-methyl-4-oxo-5N-piperidinothiazolidin-2-ylidene)acetic acid esters and a process for their preparation. The process provides the dextrorotatory isomers substantially free from the corresponding levorotatory isomers. Antihypertensive pharmaceutical compositions comprising the dextrorotatory esters and methods for using said compositions are also disclosed.

14 Claims, 1 Drawing Figure

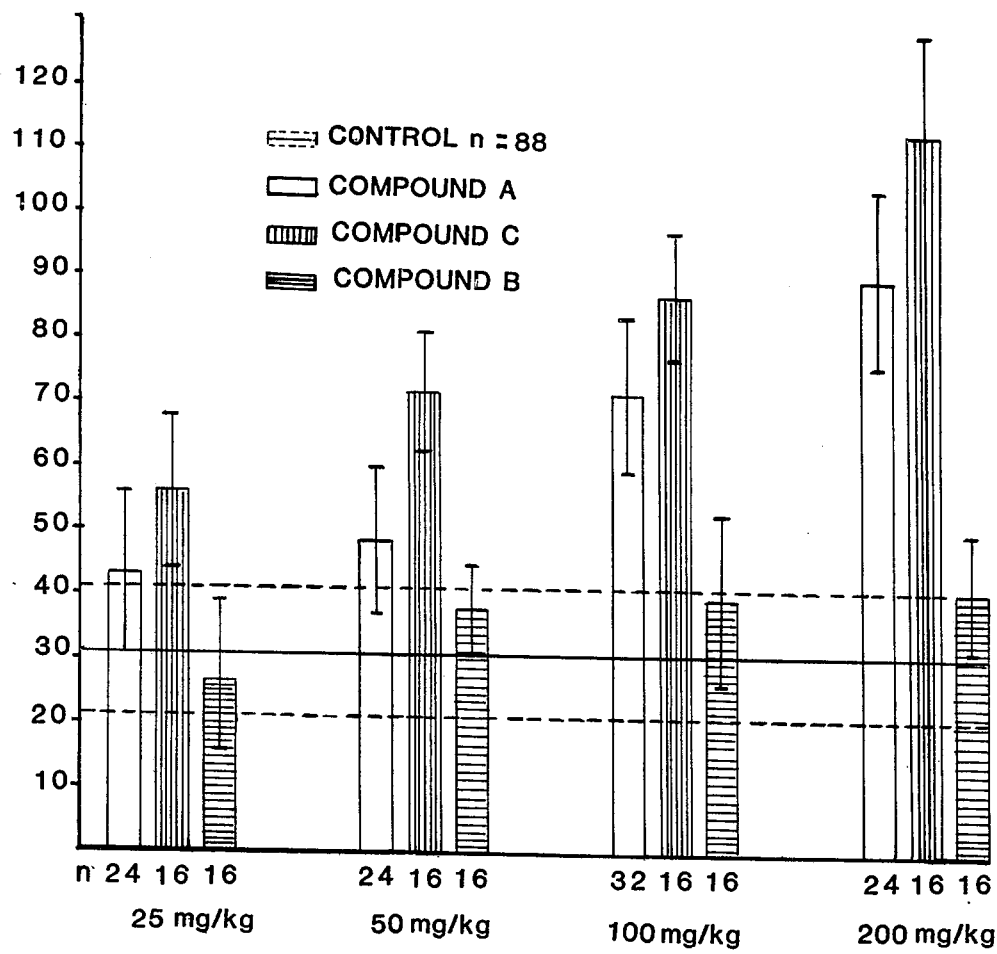

(+)-(3-METHYL-4-OXO-5N-PIPERIDINO-THIAZOLIDIN-2-YLIDENE)ACETIC ACID ESTERS, METHOD OF PREPARATION AND USE

BACKGROUND OF THE INVENTION

Ethyl (3-methyl-4-oxo-5N-piperidinothiazolidin-2-ylidene)acetate (etozoline) is a known compound [see Liebigs Ann. Chem., 665, 150(1963)] and its diuretic action has also already been described.

This compound contains an asymmetric carbon atom in the 5-position; thus, etozoline is a racemate. Because of the particular structural characteristics of etozoline, the separation of the racemate into its optically active isomers has hitherto not been carried out for certain technical reasons. Etozoline is a very weak base which does not form salts with the usual chiral acids, for example (+)-tartaric acid, (+)-dibenzoyltartaric acid and (+)-camphorsulphonic acid. Thus, this racemate has not been separated by known methods.

Esterification of the known, optically-active (+)-(3-methyl-4-oxo-5N-piperidinothiazolidin-2-ylidene)-acetic acid [(+)-ozolinone (see Federal Republic of Germany Patent Specification No. 26 58 858)] also cannot be carried out with agents which can be used on a large scale because it racemizes under the esterification conditions. Thus, for example, (+)-ozolinone racemizes to an extent of 15% in 0.1N hydrochloric acid in less than 1 hour. Even in chloroform, in the same period of time, the degree of racemization which occurs is about 10%.

We have now surprisingly found that (+)-ozolinone can be esterified without racemization via the acid chloride. Thus, pure (+)-etozoline is obtained when a solution of the free (+)-carboxylic acid [(+)-ozolinone] is quickly mixed at a low temperature with an excess of a compound chosen from among thionyl chloride phosphorous oxychloride, phosphorous pentachloride and phosphorous trichloride; thereafter anhydrous ethanol, also in excess, is added thereto. In the case of this method of esterification, surprisingly, no racemization takes place and pure (+)-etozoline is obtained.

The method according to the present invention has also proved to be useful for the preparation of other optically pure esters of ozolinone and permits the large scale preparation of these optically-active compounds in an especially favorable one-pot process.

SUMMARY OF THE INVENTION

The present invention relates to the dextrorotatory isomer, substantially free from the levorotatory isomer, of an optically-active compound of the general formula I:

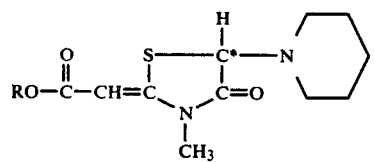

in which R is a straight- or branched-chain alkyl group containing from 1 to 4 carbon atoms and *C denotes an asymmetric carbon atom.

The invention also relates to a process for the preparation of the optically-active dextrorotatory isomer I, substantially free from the corresponding levorotatory isomer, wherein (+)-ozolinone of formula II:

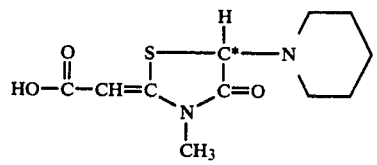

is rapidly mixed, in a solvent which is inert under the reaction conditions with regard to racemization, at a temperature of from about −10° C. to about 40° C. with an excess of a compound chosen from among thionyl chloride, phosphorous oxychloride, phosphorous pentachloride, and phosphorous trichloride and after a reaction period of about 10 to about 60 minutes, an excess of an alcohol of the general formula III:

R—OH (III)

in which R has the same meaning as above, is added thereto, the reaction mixture is allowed to react, optionally with slight cooling, whereafter the desired product is isolated.

The invention also relates to pharmaceutical compositions which comprise an antihypertensive-effective amount of a dextrorotatory isomer of a compound of the formula I.

The invention also relates to a method for treating hypertension in a mammal which method comprises administering to a mammal in need thereof an antihypertensive effective amount of a dextrorotary isomer of a compound of formula I.

DESCRIPTION OF THE INVENTION

The dextrorotatory isomers of the compounds of formula I are prepared, substantially free from the corresponding levorotatory isomers, in the following manner:

The dextrorotatory isomer of the compound of formula II [(+)-ozolinone] is first dissolved in a solvent. The solvents used for the reaction can be all solvents which are inert under the reaction conditions with regard to racemization, especially preferred are chlorinated hydrocarbons, such as dichloromethane and chloroform. The addition of a dipolar, aprotic solvent, such as hexamethylphosphoric acid triamide, has also proved to be useful. The dissolved carboxylic acid is mixed at a temperature of from about −10° C. to about 40° C. and preferably at ambient temperature, optionally with cooling, with an excess of a compound chosen from among thionyl chloride, phosphorous oxychloride, phosphorous pentachloride and phosphorous trichloride. Thereafter, the reaction is allowed to continue for 15 to 60 minutes. Subsequently, a comparatively large excess (up to 50 equivalents) of the alcohol component of general formula III is added thereto; and the reaction mixture is then allowed to stir for about 30 minutes at 10° C. to 25° C.

The reaction mixture is then extracted with cold dilute ammonia solution in order to remove inorganic acids, alcohol and unreacted starting carboxylic acid. The organic phase is subsequently dried, the solvent is distilled off and the residue is crystallized, by means of the addition of a solvent in which the dextrorotatory isomers of the compounds of general formula I are sparingly soluble, for example benzene or cyclohexane.

This process can, of course, be modified with regard to the reaction conditions but the above-described embodiment of the process has proved to be especially advantageous.

The pharmacological investigation of the alkyl esters of (+)-ozolinone according to the present invention gave completely unexpected results in that the diuretic activity present in the racemate is not present in the pure dextrorotatory isomers. However, the pure dextrorotatory isomers nevertheless were surprisingly found to possess a strong antihypertensive action. Hitherto, even in potent diuretics, a more or less strongly antihypertensive action has admittedly been found. This antihypertensive effect is generally regarded as a causal consequence of the anti-edematous properties of potent diuretics normalizing the electrolyte equilibrium. It has also previously been observed in the case of etozoline that, even at subdiuretic doses, an antihypertensive effect occurs (cf. Federal Republic of Germany Patent Specification No. 25 32 180). However, from these findings, it could only have been concluded that, even in the case of pure optical isomers, both directions of activity would still be present. Conclusions regarding separately present mechanisms were hitherto not possible.

The finding according to the present invention is not only scientifically interesting and without parallel in the prior art but also opens up a way to a completely new type of antihypertensively-acting compounds which are characterized by no longer possessing diuretic side effects. The previous risks which regularly accompanied the treatment of hypertension with potent diuretics, namely, electrolyte imbalance, heartcirculation stressing or hemoconcentration, can now be completely avoided by the use of the compounds according to the present invention.

According to the present invention, it is now possible for the first time to separate the antihypertensive component of the activity profile of a potent class of diuretics and to make it useful in pure form. This advance is all the more valuable since previous attempts to influence the activity profile of racemic diuretics by racemate splitting did not produce any significant results. Therefore, they were regarded as being unimportant in practice [see Arzneimittelforschung, 17, 657(1967)].

The present invention provides a solution to a long existing problem and thus provides the possibility for the therapy of various forms of hypertension with a new type of antihypertensive medicament which is free from the side effects of the known diuretics [cf. Drugs, 14, 446(1977)]. Since the medicinal therapy of high blood pressure is planned for very long periods of time and, not unusually, must be carried out for many years, it is particularly important to employ medicaments without side effects. Only in this way can it be ensured that the treatment can be carried out without interruption and free of disturbance. Therefore, the exclusively antihypertensively-acting dextrorotatory isomers of the compounds of general formula I represent a significant technical advance.

The following pharmacological investigations show the exclusive antihypertensive properties of the pure dextrorotatory isomers of the compounds according to the present invention:

Pharmacological investigations

The racemic compounds of general formula I showed, in the case of pharmacological testing, strong diuretic and saluretic properties and had a good antihypertensive activity. These findings have already been published for the compound in which R is ethyl (etozolin) [see Arzneimittelforschung/Drug Research, (II), No. 9a, 1745(1977)].

The diuretic action of the compounds of formula I is completely limited to the levorotatory enantiomers, the dextrorotatory enantiomers being completely inactive with regard to diuresis. Indeed, the dextrorotatory enantiomers even exhibit a furosemide antagonistic action to the kidneys.

In the case of rats with renovascular high blood pressure, the levorotatory enantiomers, in the diuretically effective dosage range, lower somewhat, as is to be expected, the average blood pressure of the hypertensive animals because of the saluretic action.

However, the diuretically absolutely ineffective pure dextrorotatory enantiomers possess a considerably stronger antihypertensive action.

Thus, with the pure dextrorotatory enantiomers of general formula I, there is provided a completely new principle for the treatment of hypertension which, due to the low toxicity and the absence of side effects, possesses a great degree of therapeutic certainty.

1. Acute toxicity (a) Methodology

The experimental animals used were male and female rats of the SIV 50 strain with a body weight of 115 to 170 g and of 100 to 160 g, respectively. All the animals were fasted for 20 hours before the commencement of the experiments, water was available ad libitum. There were 10 animals in each dosage group. The test substances were administered intragastrally with a metal probe in the form of 1% tragacanth slurry suspensions (4 ml/100 g of body weight).

The animals were observed over a period of time of 7 days. For the calculation of the $LD_{50}$ with the related confidence limits, use was made of Weber's probit analysis (see Grundriss der Biologischen Statistik, pub. Gustav Fischer Verlag, Jena, 1–72).

(b) Results

The following compounds were investigated or compared on the basis of values published in the literature:

Compound A: ethyl (±)-(3-methyl-4-oxo-5N-piperidinothiazolidin-2-ylidene)acetate (etozolin)

Compound B: ethyl (+)-(3-methyl-4-oxo-5N-piperidinothiazolidin-2-ylidene)acetate Compound C: ethyl (−)-(3-methyl-4-oxo-5N-piperidinothiazolidin-2-ylidene)acetate Compound D: 6-chloro-3,4-dihydro-2H-1,2,4-benzothiadiazine-7-sulphonamide 1,1-dioxide (hydrochlorothiazide)

Compound E: 5-(aminosulfonyl)-4-chloro-2-[(2-furanylmethyl)amino]benzoic acid (furosemide)

Compound F: [2,3-dichloro-4-(2-methylene-1-oxobutyl)phenoxy]acetic acid (ethacrynic acid)

Compound G: 6-phenyl-2,4,7-pteridinetriamine (triamterene).

The $LD_{50}$ values of Compounds A and B are summarized in the following Table I;

TABLE I

| Compound | Sex (rat) | $LD_{50}$ mg/kg intragastral | confidence limits mg/kg $p = 0.05$ | |
|---|---|---|---|---|
| | | | lower | upper |
| A | male | 11,040 | 9,380 | 13,000 |

TABLE I-continued

| Compound | Sex (rat) | LD$_{50}$ mg/kg intragastral | confidence limits mg/kg p = 0.05 lower | upper |
|---|---|---|---|---|
| | female | 10,250 | 9,260 | 11,350 |
| B | male | 3,646 | 3,083 | 4,161 |
| | female | 4,227 | 3,590 | 5,192 |

For the purpose of comparison, the literature values (cf. Meng-Loew, Diuretika, pub. Georg Thieme Verlag, Stuttgart, 1974, p. 177) for the known diuretic compounds D to G are set out in the following Table II:

TABLE II

| Compound | Sex (mice) | LD$_{50}$ mg/kg |
|---|---|---|
| D | male | 3,080 |
| E | male | 4,600 |
| F | male | 600 |
| G | male | 450 |

As can be seen from Table I, Compound B is more toxic than Compound A but, nevertheless, since it has an LD$_{50}$ greater than 2 g/kg body weight, it is extraordinarily nontoxic.

2. Diuresis in awake rats (a) Methodology

The experimental animals used were male rats of the SIV 50 strain which were kept under constant conditions. Feed was removed 36 hours before the commencement of the experiments but water was available until just before the commencement of the experiment.

The test substances were administered intragastrally as suspensions in 1% tragacanth slurry which has been prepared with a 0.2% sodium chloride solution (1 ml/100 g body weight). In addition, the animals were given intragastrally 4 ml/100 g body weight a 0.2% sodium chloride solution. The animals were kept individually in metabolic cages in order to determine the urine volumes within the first 4 hours.

(b) Results

In the FIG. 2, there are graphically illustrated the urine-time volumes, the average value with standard deviations of 88 control animals being shown parallel to the abscissae:

It can be seen from the Figure that Compounds A and C are diuretically effective in a dosage dependent manner and that Compound B does not possess any diuretic action at all.

3. Renovascular high blood pressure (a) Methodology

The antihypertensive properties were investigated in rats which, after experimental ligature of the kidney blood flow, had developed a renovascular high blood pressure.

The experimental animals used were male rats of the SIV 50 strain which, under ether narcosis, had been monolaterally nephrectomised and the contralateral renal arteries of which had been stenosed 2 days later with the help of silver clips. After 6 to 8 weeks, these animals developed a high blood pressure. The blood pressure measurement took place bloodlessly on the root of the tail of the animals.

The test substances were administered intragastrally once daily as tragacanth slurry suspensions for 33 days.

(b) Results

In the following Table III, there are given the average blood pressure values before, during and after the treatment:

TABLE III

| Renovascular high blood pressure | | | | |
|---|---|---|---|---|
| 100 mg/kg i.g. | control | A | C | B |
| before treatment | 190 | 197 | 191 | 189 |
| 6th day of treatment | 183 | 187 | 177 | 170 |
| 13th day of treatment | 195 | 175 | 173 | 169 |
| 20th day of treatment | 207 | 175 | 176 | 164 |
| 2nd day after treatment | 197 | 195 | 201 | 190 |
| 200 mg/kg i.g. | control | A | C | B |
| before treatment | 185 | 187 | 192 | 185 |
| 10th day of treatment | 185 | 171 | 178 | 159 |
| 17th day of treatment | 188 | 182 | 176 | 150 |
| 33rd day of treatment | 196 | 174 | 164 | 156 |
| 8th day after treatment | 182 | 182 | 190 | 182 |

It can be seen from Table III that, for example, the diuretically inactive Compound B possesses the strongest antihypertensive action and that this effect is dosage dependent.

The present invention also provides pharmaceutical compositions containing at least one dextrorotatory isomer of a compound of general formula I, in admixture with a solid or liquid pharmaceutical diluent or carrier.

The dextrorotatory isomers of the compounds of general formula I can be administered in liquid or solid form. Liquid forms are, in particular, prepared on an aqueous basis and contain conventional additives, such as stabilizing agents, solubilizing agents and/or buffers. Examples of such additives include ethanol, complex formers (such as ethylenediaminetetraacetic acid and the nontoxic salts thereof), tartrate and citrate buffers and high molecular weight polymers (for example liquid polyethylene oxide) for viscosity regulation. Solid carrier materials include, for example, starch, lactose, mannitol, methyl cellulose, talc, highly dispersed silicic acids, high molecular weight fatty acids (for example stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening materials.

The dosage depends upon the nature and severity of the disease to be treated. Generally, the individual dose is from 20 to 400 mg of the pure dextrorotatory isomer of a compound of formula I.

The following Examples are given for the purpose of illustrating the present invention:

EXAMPLE 1

Ethyl (+)-(3-methyl-4-oxo-5N-piperidinothiazolidin-2-ylidene)acetate 25.6 g (0.1 mol) (+)-(3-methyl-4-oxo-5N-piperidinothiazolidin-2-ylidene)acetic acid is dissolved in a mixture of 500 ml chloroform and 100 ml hexamethylphosphoric acid triamide (HMPT). Then, with the exclusion of moisture, at ambient temperature and with efficient and rapid stirring, 23.8 g (0.2 mol) thionyl chloride is added thereto and, after 15 minutes, 36.8 g (0.8 mol) anhydrous ethanol is also added thereto. After a further 30 minutes, 500 ml dilute aqueous ammonia solution is added. The chloroform phase is then separated and extracted four times with 500 ml amounts of dilute aqueous ammonia solution. The chloroform phase is dried with 50 g anhydrous magnesium sulphate, evaporated on a rotary evaporator and the residue crystallized by the addition of 200 ml petroleum ether. The crystals are filtered with suction and recrystallized from 200 ml cyclohexane. The almost colorless crystals obtained are dried at 50° C. There is obtained 19.5 g (69% of theory) ethyl (+)-(3-methyl-4-oxo-5N-piperidinothiazolidin-2-ylidene)acetate; mp 131° C. $[\alpha]_D^{23} = +224°$ (c=0.5 in chloroform).

EXAMPLE 2

Ethyl (+)-(3-methyl-4-oxo-5N-piperidinothiazolidin-2-ylidene)acetate 768 g (3 mol) (+)-(3-Methyl-4-oxo-5N-piperidinothiazolidin-2-ylidine)acetic acid is dissolved in 7 liters dichloromethane. 428 g (3.6 mol) Thionyl chloride (262 ml) is allowed to run all at once into this solution, while stirring. The temperature thereby increases from 18° C. to 27° C. The reaction mixture is cooled to 20° C. and stirred for 30 minutes at this temperature. Subsequently, 2760 g (60 mol) anhydrous ethanol (3500 ml) is allowed to run in all at once, the temperature thereby increasing to 26° C. The reaction mixture is again cooled to 20° C. and stirred for 30 minutes. Subsequently, the reaction mixture is extracted once with 9 liters of a mixture of 1.5 liters concentrated aqueous ammonia solution, 3 kg ice and 4.5 liters water and four times with 4 liter amounts of water. The dichloromethane phase is dried with 200 g magnesium sulphate, filtered and evaporated on a rotary evaporator. The addition of 6 liters of petroleum ether causes the product to crystallize. The crystals are filtered with suction, thereafter washed with 500 ml benzene and dried at 45° C. There is obtained 528 g (62.1% of theory) ethyl (+)-(3-methyl-4-oxo-5N-piperidinothiazolidin-2-ylidene)acetate; mp 130.8° C.; $[\alpha]_D^{23} = +226.5°$ (c=1 in chloroform).

The following compounds are obtained in an analogous manner:

n-propyl (+)-(3-methyl-4-oxo-5N-piperidino-thiazolidin-2-ylidene)acetate isopropyl (+)-(3-methyl-4-oxo-5N-piperidinothiazolidin-2-ylidene)acetate n-butyl (+)-(3-methyl-4-oxo-5N-piperidinothiazolidin-2-ylidene)acetate isobutyl (+)-(3-methyl-4-oxo-5N-piperidinothiazolidin-2-ylidene)acetate t-butyl (+)-(3-methyl-4-oxo-5N-piperidinothiazolidin-2-ylidene)acetate.

EXAMPLE 3

Methyl (+)-(3-methyl-4-oxo-5N-piperidinothiazolidin-2-ylidene)acetate 153 g (0.6 mol) (+)-(3-Methyl-4-oxo-5N-piperidinothiazolidin-2-ylidene)acetic acid is dissolved in 1.53 liters dichloromethane and mixed all at once, while stirring, with 107 g (0.9 mol) thionyl chloride (about 66 ml, d=1.63). The reaction mixture is stirred for 30 minutes at 20° C. and then 768 g (24 mol) methanol (967 ml) is added all at once. The reaction mixture is then stirred for 30 minutes at 20° C. The organic phase is subsequently washed with 2.5 liters dilute aqueous ammonia solution (300 ml concentrated ammonium hydroxide in water) and then washed three times with 2.5 liter amounts of water. The dichloromethane phase is dried with anhydrous sodium sulphate, evaporated in a rotary evaporator and the residue obtained is crystallized from 1 liter cyclohexane. The crystals are filtered with suction and dried at 60° C. There is obtained 124 g (76.7% of theory) methyl (+)-(3-methyl-4-oxo-5N-piperidinothiazolidin-2-ylidene)acetate; mp 126.1° C.; $[\alpha]_D^{23} = +239°$ (c=0.5 in chloroform).

EXAMPLE 4

Methyl (+)-(3-methyl-4-oxo-5N-piperidinothiazolidin-2-ylidene)acetate 30 g (0.117 mol) (+)-(3-Methyl-4-oxo-5N-piperidinothiazolidin-2-ylidene)acetic acid is dissolved in a mixture of 600 ml dichloromethane and 120 ml hexamethylphosphoric acid triamide and, while stirring at 20° C., is mixed all at once with 27.8 g (0.234 mol) thionyl chloride (d=1.63; about 17.1 ml). The temperature thereby increasing to 26° C. The reaction mixture is cooled to 20° C., stirred for 30 minutes and then mixed with 37.5 g (1.17 mol) anhydrous methanol and again cooled to 20° C. After 30 minutes, the reaction mixture is extracted once with 1 liter dilute aqueous ammonia solution (100 ml concentrated ammonium hydroxide and water) and five times with 1 liter amounts of water. The dichloromethane phase is dried with anhydrous sodium sulphate, evaporated in a rotary evaporator and the residue crystallized from 300 ml petroleum ether. There is obtained 25.8 g (81.6% of theory) methyl (+)-(3-methyl-4-oxo-5N-piperidinothiazolidin-2-ylidene)-acetate; mp 125.8° C.; $[\alpha]_D^{23} = +239°$ (c=0.5 in chloroform).

EXAMPLE 5

Ethyl (−)-(3-methyl-4-oxo-5N-piperidinothiazolidin-2-ylidene)acetate 25.6 g. (0.1 mol) (−)-(3-Methyl-4-oxo-5N-piperidinothiazolidin-2-ylidene)acetic acid is dissolved in a mixture of 500 ml dichloromethane and 100 ml hexamethylphosphoric acid triamide. With the exclusion of moisture and at ambient temperature and with efficient rapid stirring, 23.8 g (0.2 mol) thionyl chloride is added thereto and, after 15 minutes, 36.8 g (0.8 mol) anhydrous ethanol is also added. After a further 30 minutes, 500 ml dilute aqueous ammonia solution is added and the phases are separated. The dichloromethane phase is further extracted four times with 500 ml amounts of dilute aqueous ammonia solution, dried with 50 g anhydrous magnesium sulphate and evaporated on a rotary evaporator. The residue is crystallized by the addition of 200 ml petroleum ether. The crystals are filtered with suction and recrystallized from cyclohexane. The almost colorless crystals are dried at 50° C. There is obtained 19.5 g (69% of theory) ethyl (−)-(3-methyl-4-oxo-5N-piperidinothiazolidin-2-ylidene)acetate; mp 130° C.; $[\alpha]_D^{23} = -229.8°$ (c=0.5 in chloroform).

EXAMPLE 6

Ethyl (+)-(3-methyl-4-oxo-5N-piperidinothiazolidin-2-ylidene)acetate 25.6 g (0.1 mol) (+)-(3-Methyl-4-oxo-5N-piperidinothiazolidin-2-ylidene)acetic acid is dissolved in 228 ml dichloromethane with stirring. 22.8 g (0.11 mol) phosphorous pentachloride in 256 ml dichloromethane is allowed to run rapidly into this solution while stirring. The temperature is maintained at 30° C. The mixture is then cooled to 20° C. and stirred for 30 minutes at this temperature. Subsequently, 291 ml (5 mol) anhydrous ethanol is allowed to run in at once, the temperature thereby increases to 28° C. The reaction mixture is again cooled to 20° C. and is stirred for 30 minutes. Subsequently, the reaction mixture is extracted once with 200 ml aqueous ammonia and four times with 200 ml amounts of water. The dichloromethane phase is dried with sodium sulfate and then evaporated. The residue is recrystallized from 200 ml petroleum ether. There is obtained 24.0 g (84.4% of theory) ethyl (+)-(3-methyl-4-oxo-5N-piperidinothiazolidin-2-ylidene)-acetate; mp 129.4° C.; $[\alpha]_D^{RT} = +226.1°$ (c=1 in chloroform).

EXAMPLE 7

Ethyl (+)-(3-methyl-4-oxo-5N-piperidinothiazolidin-2-ylidene)acetate

The reaction of Example 6 is carried out with 0.01 mol phosphorus oxychloride under exactly the same reaction conditions. There is obtained 710 mg (25% of theory) ethyl (+)-(3-methyl-4-oxo-5N-piperidinothiazolidin-2-ylidene)acetate, mp 107.5° C.; $[\alpha]_D^{RT} = +208°$ (c=1 in Chloroform). This product contains impurities consisting of the anhydride.

EXAMPLE 8

Ethyl (+)-(3-methyl-4-oxo-5N-piperidinothiazolidin-2-ylidene)acetate

The reaction of Example 6 is carried out with 0.01 mol phosphorous trichloride under exactly the same reaction conditions. There is obtained 110 mg (3.8% of theory); mp 120.6° C.; $[\alpha]_D^{RT} = +211°$ (c=1 in chloroform).

We claim:

1. A dextrorotatory isomer, substantially free from the levorotatory isomer, of an optically-active compound of the formula I:

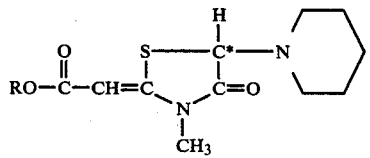

in which R is a straight- or branched-chain alkyl group containing from 1 to 4 carbon atoms and *C denotes an asymmetric carbon atom.

2. Dextrorotatory isomers according to claim 1, wherein R is a methyl or ethyl group.

3. Ethyl (+)-(3-methyl-4-oxo-5N-piperidinothiazolidin-2-ylidene)acetate.

4. n-Propyl (+)-(3-methyl-4-oxo-5N-piperidinothiazolidin-2-ylidene)acetate.

5. Isopropyl (+)-(3-methyl-4-oxo-5N-piperidinothiazolidin-2-ylidene)acetate.

6. n-Butyl (+)-(3-methyl-4-oxo-5N-piperidinothiazolidin-2-ylidene)acetate.

7. Isobutyl (+)-(3-methyl-4-oxo-5N-piperidinothiazolidin-2-ylidene)acetate.

8. t-Butyl (+)-(3-methyl-4-oxo-5N-piperidinothiazolidin-2-ylidene)acetate.

9. Methyl (+)-(3-methyl-4-oxo-5N-piperidinothiazolidin-2-ylidene)acetate.

10. A process for the preparation of the dextrorotatory isomers defined in claim 1, wherein (+)-ozolinone of the formula II

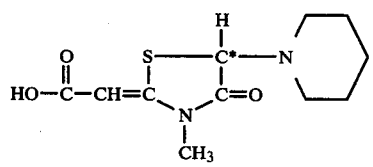

is rapidly mixed, in a solvent which is inert under the reaction conditions with regard to racemization, at a temperature of from about −10° C. to about 40° C. with an excess of a compound chosen from among thionyl chloride, phosphorous oxychloride, phosphorous pentachloride and phosphorous trichloride and after a reaction period of about 10 to about 60 minutes, an excess of an alcohol of the general formula ROH, in which R has the same meaning as in claim 1, is added thereto and the reaction mixture is allowed to react, optionally with slight cooling, whereafter the desired product is isolated.

11. The process according to claim 10, wherein the solvent used is a chlorinated hydrocarbon containing a dipolar aprotic solvent.

12. The process according to claim 10, wherein the reaction is carried out at ambient temperature.

13. A pharmaceutical composition comprising an antihypertensive effective amount of a dextrorotatory isomer according to claim 1, together with a suitable pharmaceutical carrier.

14. A method for treating hypertension in a mammal which method comprises administering to a mammal, in need thereof, an antihypertensive effective amount of a composition as claimed in claim 13.

* * * * *